US010032005B2

(12) United States Patent
Fauci

(10) Patent No.: US 10,032,005 B2
(45) Date of Patent: *Jul. 24, 2018

(54) METHODS AND SYSTEMS TO SECURE CONTROL AND ENHANCE MEDICATION ADHERENCE

(71) Applicant: GEN-9, INC., Mountain View, CA (US)

(72) Inventor: Mark A. Fauci, Patchogue, NY (US)

(73) Assignee: GEN-9, INC., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,005

(22) Filed: May 10, 2016

(65) Prior Publication Data

US 2016/0253479 A1 Sep. 1, 2016

Related U.S. Application Data

(63) Continuation of application No. 13/854,199, filed on Apr. 1, 2013, now Pat. No. 9,361,431.

(60) Provisional application No. 61/619,545, filed on Apr. 3, 2012.

(51) Int. Cl.
| | |
|---|---|
| G06F 17/00 | (2006.01) |
| G06F 19/00 | (2018.01) |
| G07F 17/00 | (2006.01) |
| A61J 7/00 | (2006.01) |

(52) U.S. Cl.
CPC ........ *G06F 19/3462* (2013.01); *A61J 7/0076* (2013.01); *G07F 17/0092* (2013.01)

(58) Field of Classification Search
None
See application file for complete search history.

(56) References Cited

U.S. PATENT DOCUMENTS

| | | | | |
|---|---|---|---|---|
| 5,472,113 A | * | 12/1995 | Shaw | A61J 7/0084 221/15 |
| 6,611,733 B1 | * | 8/2003 | De La Huerga | A61J 1/1437 700/235 |
| 7,263,411 B2 | * | 8/2007 | Shows | G06F 19/3462 221/2 |

(Continued)

*Primary Examiner* — Prasad V Gokhale
(74) *Attorney, Agent, or Firm* — Kilpatrick Townsend & Stockton, LLP

(57) ABSTRACT

Embodiments of the invention provide systems and methods to provide safe, secure and accurate point-to-point delivery of prescription and non-prescription drugs in the long-term home care or ambulatory care environment. More specifically, embodiments of the present invention provide for a low-cost, easy-to-use system comprised of a secure drug dispensing unit and medication enclosure combined with wireless connectivity and software based on smart mobile phone technology. Such systems and methods, referred to herein as a Secure, Control, and Enhance Medication Adherence (SCEMA) system, can mitigate the aforementioned risks associated with the use of prescription and non-prescription drugs. These risks can be significantly reduced for the elderly in the homecare environment, as well as the general public, without disrupting, or a significantly increasing the cost, to the existing prescription and non-prescription drug distribution infrastructure. In addition, the SCEMA system can provide a powerful platform for drug research.

11 Claims, 5 Drawing Sheets

(56) References Cited

U.S. PATENT DOCUMENTS

| | | | | |
|---|---|---|---|---|
| 7,444,204 B2* | 10/2008 | Chirnomas | G07F 9/02 | 221/2 |
| 8,180,485 B2* | 5/2012 | Reckelhoff | A61G 12/001 | 700/242 |
| 8,196,774 B1* | 6/2012 | Clarke | A61J 7/0409 | 221/13 |
| 8,494,663 B2* | 7/2013 | Lamoree | B64D 11/003 | 200/17 R |
| 8,757,435 B2* | 6/2014 | Van Oort | B65D 83/0472 | 221/197 |
| 8,957,328 B2* | 2/2015 | Rogers | G01G 19/44 | 128/922 |
| 9,361,431 B2 | 6/2016 | Fauci | | |
| 2004/0148055 A1* | 7/2004 | Shoenfeld | A61G 12/001 | 700/237 |
| 2005/0240305 A1* | 10/2005 | Bogash | G06F 19/3462 | 700/242 |
| 2006/0071011 A1* | 4/2006 | Varvarelis | A61J 7/0481 | 221/9 |
| 2009/0167531 A1* | 7/2009 | Ferguson | G06F 19/3462 | 340/572.1 |
| 2009/0259486 A1* | 10/2009 | Burg | G06F 19/3418 | 705/2 |
| 2010/0164716 A1* | 7/2010 | Estevez | G06F 19/3462 | 340/540 |
| 2010/0176950 A1* | 7/2010 | Bartholf | G07F 9/026 | 340/572.7 |
| 2012/0241227 A1* | 9/2012 | Rogers | G01G 19/44 | 177/1 |
| 2013/0066463 A1* | 3/2013 | Luoma | A61J 1/035 | 700/232 |
| 2014/0277702 A1* | 9/2014 | Shaw | G06F 19/3462 | 700/232 |
| 2014/0324216 A1* | 10/2014 | Beg | G06O 20/322 | 700/232 |

* cited by examiner

METHODS AND SYSTEMS TO SECURE CONTROL AND ENHANCE MEDICATION ADHERENCE

CROSS-REFERENCES TO RELATED APPLICATIONS

The present application is a continuation application of U.S. patent application Ser. No. 13/854,199 filed on Apr. 1, 2013 by Fauci and entitled "Methods and Systems to Secure Control and Enhance Medication Adherence," which claims benefit under 35 USC 119(e) of U.S. Provisional Application No. 61/619,545, filed on Apr. 3, 2012 by Fauci and entitled "Secure Control and Enhance Medication Adherence (SCEMA) Systems," of which the entire disclosures are incorporated herein by reference for all purposes.

BACKGROUND OF THE INVENTION

Embodiments of the present invention relate generally to methods and systems for management of medications and more particularly to method and systems to provide safe, secure and accurate point-to-point delivery of prescription and non-prescription drugs.

Multiple, potential risks or complications that exist in the administration of medicines are derived from patient, provider, pharmacy, and/or system level failures. These risks are significantly mitigated in the acute care setting through the use of automated pharmacy technologies that include unit dose packaging systems that match bar coded medication packets to patient's bar coded wrist bands, thereby establishing positive patient identification and electronically verifying the medication at the bedside. The same risks of medication errors found in the acute care setting are substantially magnified in the home or ambulatory care setting due to the lack of similar point-to-point medication delivery technology, as well as the absence of direct medical supervision. These risks have been shown to lead to increases in hospital readmission rates, long-term care admissions, morbidity and mortality events. According to the National Institute on Drug Abuse (NIDA), currently available technologies and methods to address these problems are inadequate.

One quarter of the prescription drugs sold in the United States are used by the elderly, often for problems such as chronic pain, insomnia, and anxiety. Multiple potential risks or complications that ordinarily exist in the administration of medicines in an institutionalized care setting are significantly magnified in the home care environment. If not adequately addressed and managed these risks have been shown to lead to increases in morbidity and mortality. Home-based elderly are perhaps among the most vulnerable population in this regard. For example, Medication Adherence (MA) by the elderly is often as low as 26% and contributes to limiting the achievement of therapeutic goals. The odds of good health outcomes are nearly three times lower for patients who do not adhere to recommended therapies than for patients who follow provider recommendations. Low MA increases patient and provider frustration and can increase health care costs, including avoidable hospitalizations. For older adults, MA difficulties may account for 10 to 25% of hospital and nursing home admissions, or re-admissions, and not only exacerbates disease severity but can cause fatalities. Approximately 125,000 Americans die annually due to poor MA. The estimated annual cost of patients not taking their medications as prescribed is approaching $290 billion.

Another overlapping issue is Adverse Drug Reactions (ADR), which some researchers believe increases exponentially with the number of medications taken. ADR among the general population is estimated to be between the fourth and sixth leading cause of death in the U.S. Many studies from around the world show a correlation between increasing age and the ADR rate with the most recent studies indicating that the ADR rate for the elderly in the U.S. and Europe was 20% greater than in studies carried out in general medical settings.

Prescription Drug Diversion and Abuse (PDDA), are large and rapidly growing problems in the U.S. health care delivery system. Abuse of several categories of prescription drugs has increased markedly in the United States in the past decade and has now reached alarming levels for certain agents, especially opioid analgesics and stimulants. This category overlaps with the preceding two in that abuse of prescription drugs, and their non-prescription counterparts, is associated with a range of factors, including dose and co-administration with other drugs. The prevalence of prescription drug abuse among the elderly may be as high as 11 percent with an increased risk among women, those who are socially isolated, subject to depression, and/or have a prior history of substance abuse. Beyond the direct risk to the elderly from PDDA, collateral risk to family members, especially teens and young adults, is growing alarmingly. According to the Drug Enforcement Agency, sixty-three percent of teens believe that prescription drugs are easy to get from friends' and family's medicine cabinets, including those of their grandparents. As of 2009 there were 7 million Americans aged 12 years and older who abused prescription drugs for non-medical purposes each month, up from 6.2 million in 2008. This represents a 13 percent increase in a single year. One in seven teens admit to abusing prescription drugs to get high and sixty percent of teens who abused prescription pain relievers did so before the age of fifteen. The number of emergency room visits attributable to pharmaceuticals alone is up 97% between 2004 and 2008. According to the Center for Disease Control, prescription drugs, including opioids and antidepressants, are responsible for more overdose deaths than "street drugs" such as cocaine, heroin, and amphetamines.

Proper disposal of unused prescription drugs has become another important public health issue as rates of PDDA, accidental poisoning, and the incidence of drugs found in the drinking water have gained more attention. As a result of the growing public awareness of this problem, and it's potentially deadly effects, local, state and federal entities are struggling with efforts to insure the safe distribution and handling of prescription medications. This includes the disposal of the unused quantities that typically accumulate in medicine cabinets. Among these efforts are proposed regulations requiring drug suppliers to collect and dispose of unused drugs, an effort being strongly resisted by the drug industry due to the complexity and high cost of implementation.

Current solutions have generally failed to address any one of these problems adequately, and certainly there are none that address all of them. Most focus on the economics of dispensing drugs at the point of care in order to facilitate convenience and/or to lower overhead costs for the distributor. Others, attempt to make drug dispensing more organized and manageable, but often result in products that are nightmarish in their complexity to setup, maintain and use. Both of these types of solutions also fail to provide the proper point-to-point security required to avoid drug diversion.

Hence, there is a need for improved methods and systems for efficiently and effectively securing, controlling, and enhancing medication adherence.

BRIEF SUMMARY OF THE INVENTION

Embodiments of the invention provide systems and methods to provide safe, secure and accurate point-to-point delivery of prescription and non-prescription drugs in the long-term home care or ambulatory care environment. More specifically, embodiments of the present invention provide for a low-cost, easy-to-use system comprised of a secure drug dispensing unit and medication enclosure combined with wireless connectivity and software based on smart mobile phone technology. Such systems and methods, referred to herein as a Secure, Control, and Enhance Medication Adherence (SCEMA) system, can mitigate the aforementioned risks associated with the use of prescription and non-prescription drugs. These risks can be significantly reduced for the elderly in the homecare environment, as well as the general public, without disrupting, or a significantly increasing the cost, to the existing prescription and non-prescription drug distribution infrastructure. In addition, the SCEMA system can provide a powerful platform for drug research.

According to one embodiment, a medication dispensing unit can comprise a processor and a memory coupled with and readable by the processor and storing a set of instructions which, when executed by the processor, cause the processor to perform a plurality of functions controlling the dispensing of medication from the medication dispensing unit, and one or more wireless transceivers coupled with the processor. The medication dispensing unit can be adapted to accept one or more removable, secure medication cartridges preloaded with medication packets and dispense the medication packets from the one or more medication cartridges under control of the plurality of functions. The medication dispensing unit can further comprise a button coupled with the processor, wherein actuation of the button causes to processor to control execution of one or more of the plurality of functions. In some cases, the button can further comprise a biometric scanner, wherein the biometric scanner reads biometric information from a user of the medication dispensing unit upon actuation of the button, and wherein at least one of the plurality of functions includes authenticating the user based on the biometric information. In some implementations, the medication dispensing unit can further comprise a display coupled with the processor and wherein one or more of the plurality of functions provide information related to the one or more functions through the display.

In use, the medication dispensing can comprise at least one removable, secure medication cartridge installed therein. The medication cartridge can comprise a memory storing information for the medication dispensing unit. The information can be related to the medication packets preloaded in the medication cartridge and an intended user of the medication. In such cases, at least one of the plurality of functions can comprise reading the information related to the medication packets preloaded in the medication cartridge and the intended user of the medication when the medication cartridge is loaded into the medication dispensing unit. In some cases, the medication packets preloaded into the medication cartridge can comprise a multi-drug regime and one or more of the plurality of functions can support dispensing of the multi-drug regime. Additionally or alternatively, the installed at least one removable, secure medication cartridge can comprise a plurality of installed medication cartridges and the medications preloaded in each of the plurality of medication cartridges can be different. In such implementations, the plurality of functions can include one or more functions for changing prescriptions for dispensing the medication based on the different preloaded medications and instructions received by the medication dispensing unit via the one or more wireless transceivers. Additionally or alternatively, the plurality of functions can include one or more functions for preventing adverse drug reactions between the different drugs, providing a notification via the one or more wireless transceivers when the medication dispensing unit detects a potential adverse drug reactions, and for receiving via the one or more wireless transceivers an override instruction permitting the dispensing of medication detected as the potential adverse drug reaction. Similarly, the plurality of functions can include one or more functions for preventing dispensing of medication in an order, schedule, or combination that creates a compatibility or interaction problem. In some cases, the medications preloaded in each of the plurality of medication cartridges can be the same, and the plurality of functions can include one or more functions for affecting a refill by switching from a primary cartridge for dispensing medication to a secondary cartridge for dispensing medication when the primary cartridge becomes empty.

In some implementations, the plurality of functions can include one or more functions for providing a reminder to a user of a schedule for taking the medication based on the information stored in the memory of the medication cartridge related to the medication packets preloaded in the medication cartridge. The plurality of functions may also include one or more functions for updating the schedule based on instructions received by the medication dispensing unit via the one or more wireless transceivers. In some cases, the plurality of functions can include one or more functions for providing a notification via the one or more wireless transceivers when the medication dispensing unit detects the medication has not been taken as scheduled. Additionally or alternatively, the plurality of functions can include one or more functions for providing a refill request via the one or more wireless transceivers when the medication dispensing unit detects the medication preloaded in the medication cartridge is low.

In some implementations, the medication dispensing unit can comprise at least one removable, secure medication cartridge installed therein. The medication cartridge can comprise a memory storing information for the medication dispensing unit. The information can be related to the medication packets preloaded in the medication cartridge and an intended user of the medication. The medication cartridge can also comprise and a barcode reader. The barcode reader can read a barcode from the medication packets and the plurality of functions can include functions for matching the authenticated user to the medication packets based on the barcode.

According to another embodiment, a secure medication cartridge can comprise a container preloaded with medication packets and a feeder mechanism within the container adapted to feed the preloaded medication packets from the container. The secure medication cartridge can further comprise a reader device adapted to read information encoded on the medication packets. The information can be related to and identifying medication stored in the medication packets. The secure medication cartridge can further comprise a memory storing information related to the medication packets preloaded in the medication cartridge and an intended user of the medication. In some cases, the secure medication cartridge can further comprising a fluid reservoir within the container. The fluid reservoir can store a liquid, the medication packets can be constructed of a material that dissolves when exposed to the liquid, and the fluid reservoir can rupture when the medication cartridge is subjected to tampering. For example, the medication packets can be constructed of polyvinyl and the fluid can be distilled water.

According to yet another embodiment, a system can comprise a medication dispensing unit comprising a processor and a memory coupled with and readable by the processor. The memory can store a set of instructions which, when executed by the processor, cause the processor to perform a plurality of functions controlling the dispensing of medication from the medication dispensing unit. The medication dispensing unit can also comprise one or more wireless transceivers coupled with the processor, and a button coupled with the processor, wherein actuation of the button causes to processor to control execution of one or more of the plurality of functions. The button can further comprise a biometric scanner, wherein the biometric scanner reads biometric information from a user of the medication dispensing unit upon actuation of the button, and wherein at least one of the plurality of functions includes authenticating the user based on the biometric information.

The system can also comprise one or more secure medication cartridges removeably mounted in the medication dispensing unit. Each one or more secure medication cartridges can comprise a container preloaded with medication packets, a feeder mechanism within the container adapted to feed the preloaded medication packets from the container, a reader device adapted to read information encoded on the medication packets related to and identifying medication stored in the medication packets, a memory storing information related to the medication packets preloaded in the medication cartridge and an intended user of the medication, and a fluid reservoir within the container. The fluid reservoir can store a liquid and the medication packets can be constructed of a material that dissolves when exposed to the liquid. The fluid reservoir can rupture when the medication cartridge is subjected to tampering.

The system can further comprising one or more patient devices communicatively coupled with the medication dispensing unit via the one or more wireless transceivers. The one or more patient devices can execute an application interfacing with the plurality of functions controlling the dispensing of medication from the medication dispensing unit. Additionally or alternatively, the system can comprise one or more servers communicatively coupled with the medication dispensing unit via the one or more wireless transceivers. The one or more servers can execute one or more applications interfacing with the plurality of functions controlling the dispensing of medication from the medication dispensing unit. Additionally or alternatively, the system can comprise one or more pharmacy systems communicatively coupled with the one or more servers. The pharmacy system can execute one or more applications interfacing with the plurality of functions controlling the dispensing of medication from the medication dispensing unit. Additionally or alternatively, the system can comprise one or more care provider devices communicatively coupled with the medication dispensing unit via the one or more wireless transceivers. The one or more care provider devices can execute an application interfacing with the plurality of functions controlling the dispensing of medication from the medication dispensing unit.

DETAILED DESCRIPTION OF THE INVENTION

Figure 1:
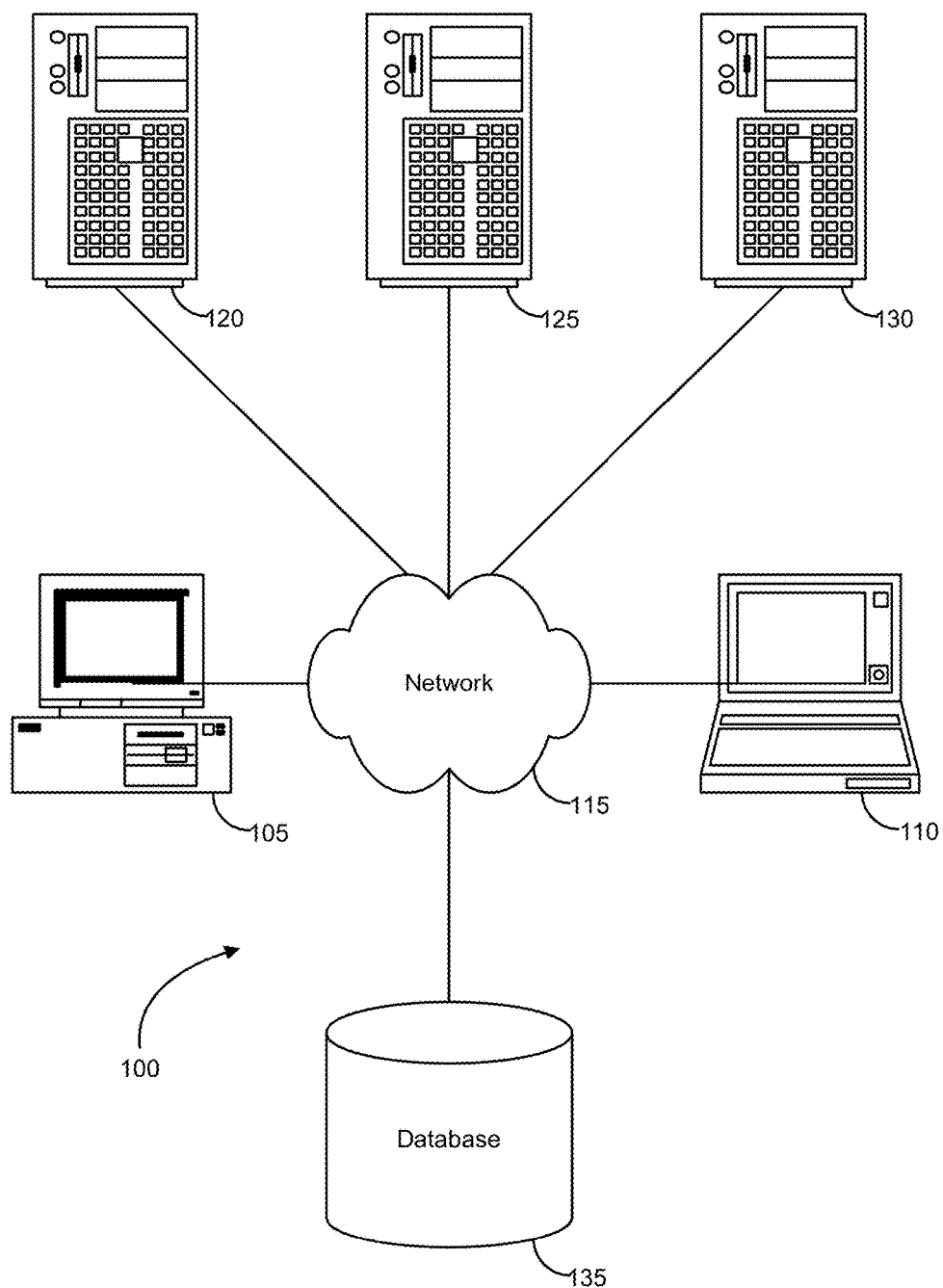
FIG. 1 is a block diagram illustrating components of an exemplary operating environment in which various embodiments of the present invention may be implemented.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the invention provide systems and methods to provide safe, secure and accurate point-to-point delivery of prescription and non-prescription drugs in the long-term home care or ambulatory care environment. More specifically, embodiments of the present invention provide for a low-cost, easy-to-use system comprised of a secure drug dispensing unit and medication enclosure combined with wireless connectivity and software based on smart mobile phone technology. Such systems and methods, referred to herein as a Secure, Control, and Enhance Medication Adherence (SCEMA) system, can mitigate the aforementioned risks associated with the use of prescription and non-prescription drugs. These risks can be significantly reduced for the elderly in the homecare environment, as well as the general public, without disrupting, or a significantly increasing the cost, to the existing prescription and non-prescription drug distribution infrastructure. In addition, the SCEMA system can provide a powerful platform for drug research.

More specifically, a SCEMA dispensing unit according to one embodiment can operate as a self-contained system that is capable of either communicating directly with a centralized server application, through an on-board cellular communication capabilities, or through another device (wireless router, PC or smart mobile device) via a Blue Tooth or WiFi connectivity. Use of wireless technology can provide and/or support a number of functions of a SCEMA system according to various embodiments including but not limited to the maintenance and updating of patient medication information (i.e. new and expired prescriptions); delivery and management of secure biometric identification (e.g., electronically scanned fingerprints); transmission of audio/visual reminders to the user, to take their medication on the prescribed schedule; updates on dispensing unit inventory and automatic refill requests; communication of drug information such as recall or potential adverse reactions; transmission of accelerometer detected attempts to forcibly open or breech the dispensing unit; localization and tracking of the dispensing unit during transport and/or in the event of diversion; in the event of diversion detection, to notify the authorities of the event time and location; and/or in the event of diversion or breech, the ability to remotely or automatically render the drugs unusable. Various additional details of embodiments of the present invention will be described below with reference to the figures.

FIG. 1 is a block diagram illustrating components of an exemplary operating environment in which various embodiments of the present invention may be implemented. The system 100 can include one or more user computers 105, 110, which may be used to operate a client, whether a dedicate application, web browser, etc. The user computers 105, 110 can be general purpose personal computers (including, merely by way of example, personal computers and/or laptop computers running various versions of Microsoft Corp.'s Windows and/or Apple Corp.'s Macintosh operating systems) and/or workstation computers running any of a variety of commercially-available UNIX or UNIX-like operating systems (including without limitation, the variety of GNU/Linux operating systems). These user computers 105, 110 may also have any of a variety of applications, including one or more development systems, database client and/or server applications, and web browser applications. Alternatively, the user computers 105, 110 may be any other electronic device, such as a thin-client computer, Internet-enabled mobile telephone, and/or personal digital assistant, capable of communicating via a network (e.g., the network 115 described below) and/or displaying and navigating web pages or other types of electronic documents. Although the exemplary system 100 is shown with two user computers, any number of user computers may be supported.

In some embodiments, the system 100 may also include a network 115. The network may can be any type of network familiar to those skilled in the art that can support data communications using any of a variety of commercially-available protocols, including without limitation TCP/IP, SNA, IPX, AppleTalk, and the like. Merely by way of example, the network 115 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth protocol known in the art, and/or any other wireless protocol); and/or any combination of these and/or other networks such as GSM, GPRS, EDGE, UMTS, 3G, 2.5G, CDMA, CDMA2000, WCDMA, EVDO etc.

The system may also include one or more server computers 120, 125, 130 which can be general purpose computers and/or specialized server computers (including, merely by way of example, PC servers, UNIX servers, mid-range servers, mainframe computers rack-mounted servers, etc.). One or more of the servers (e.g., 130) may be dedicated to running applications, such as a business application, a web server, application server, etc. Such servers may be used to process requests from user computers 105, 110. The applications can also include any number of applications for controlling access to resources of the servers 120, 125, 130.

The web server can be running an operating system including any of those discussed above, as well as any commercially-available server operating systems. The web server can also run any of a variety of server applications and/or mid-tier applications, including HTTP servers, FTP servers, CGI servers, database servers, Java servers, business applications, and the like. The server(s) also may be one or more computers which can be capable of executing programs or scripts in response to the user computers 105, 110. As one example, a server may execute one or more web applications. The web application may be implemented as one or more scripts or programs written in any programming language, such as Java™, C, C# or C++, and/or any scripting language, such as Perl, Python, or TCL, as well as combinations of any programming/scripting languages. The server(s) may also include database servers, including without limitation those commercially available from Oracle®, Microsoft®, Sybase®, IBM® and the like, which can process requests from database clients running on a user computer 105, 110.

In some embodiments, an application server may create web pages dynamically for displaying on an end-user (client) system. The web pages created by the web application server may be forwarded to a user computer 105 via a web server. Similarly, the web server can receive web page requests and/or input data from a user computer and can forward the web page requests and/or input data to an application and/or a database server. Those skilled in the art will recognize that the functions described with respect to various types of servers may be performed by a single server and/or a plurality of specialized servers, depending on implementation-specific needs and parameters.

The system 100 may also include one or more databases 135. The database(s) 135 may reside in a variety of locations. By way of example, a database 135 may reside on a storage medium local to (and/or resident in) one or more of the computers 105, 110, 115, 125, 130. Alternatively, it may be remote from any or all of the computers 105, 110, 115, 125, 130, and/or in communication (e.g., via the network 120) with one or more of these. In a particular set of embodiments, the database 135 may reside in a storage-area network ("SAN") familiar to those skilled in the art. Similarly, any necessary files for performing the functions attributed to the computers 105, 110, 115, 125, 130 may be stored locally on the respective computer and/or remotely, as appropriate. In one set of embodiments, the database 135 may be a relational database, such as Oracle 10g, that is adapted to store, update, and retrieve data in response to SQL-formatted commands.

Figure 2:
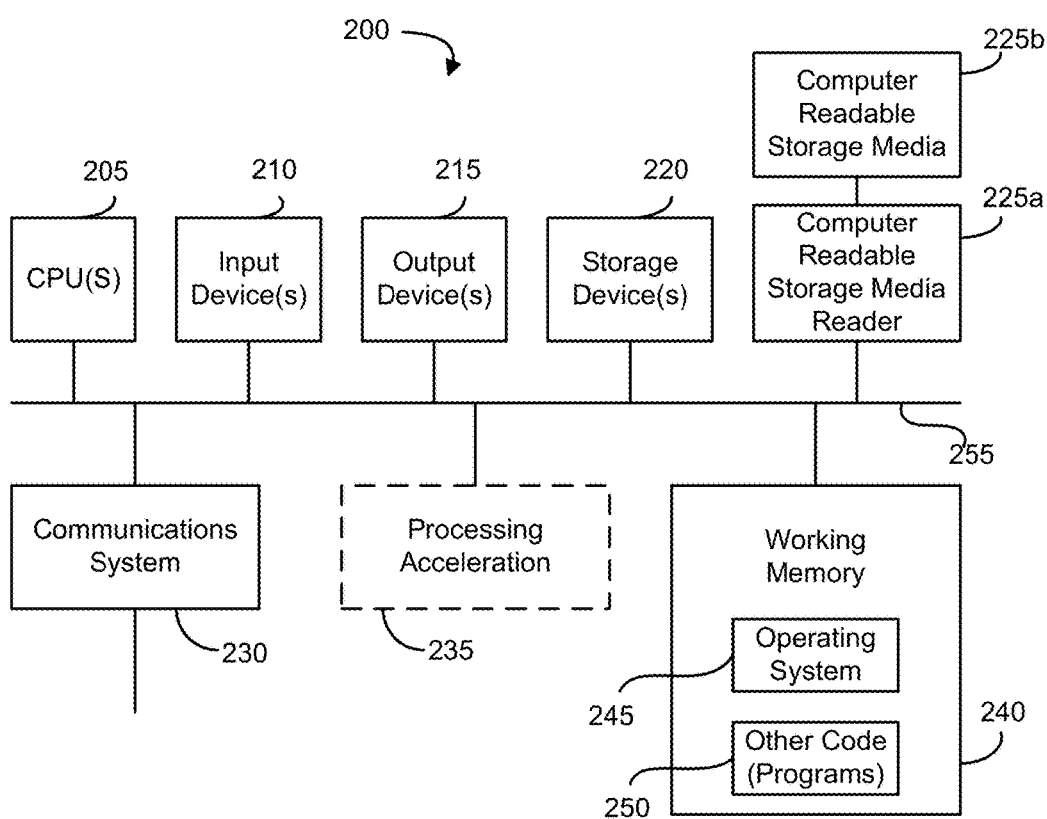
FIG. 2 is a block diagram illustrating an exemplary computer system in which embodiments of the present invention may be implemented.

FIG. 2 illustrates an exemplary computer system 200, in which various embodiments of the present invention may be implemented. The system 200 may be used to implement any of the computer systems described above. The computer system 200 is shown comprising hardware elements that may be electrically coupled via a bus 255. The hardware elements may include one or more central processing units (CPUs) 205, one or more input devices 210 (e.g., a mouse, a keyboard, etc.), and one or more output devices 215 (e.g., a display device, a printer, etc.). The computer system 200 may also include one or more storage device 220. By way of example, storage device(s) 220 may be disk drives, optical storage devices, solid-state storage device such as a random access memory ("RAM") and/or a read-only memory ("ROM"), which can be programmable, flash-updateable and/or the like.

The computer system 200 may additionally include a computer-readable storage media reader 225a, a communications system 230 (e.g., a modem, a network card (wireless or wired), an infra-red communication device, etc.), and working memory 240, which may include RAM and ROM devices as described above. In some embodiments, the computer system 200 may also include a processing acceleration unit 235, which can include a DSP, a special-purpose processor and/or the like.

The computer-readable storage media reader 225a can further be connected to a computer-readable storage medium 225b, together (and, optionally, in combination with storage device(s) 220) comprehensively representing remote, local, fixed, and/or removable storage devices plus storage media for temporarily and/or more permanently containing computer-readable information. The communications system 230 may permit data to be exchanged with the network 220 and/or any other computer described above with respect to the system 200.

The computer system 200 may also comprise software elements, shown as being currently located within a working memory 240, including an operating system 245 and/or other code 250, such as an application program (which may be a client application, web browser, mid-tier application, RDBMS, etc.). It should be appreciated that alternate embodiments of a computer system 200 may have numerous variations from that described above. For example, customized hardware might also be used and/or particular elements might be implemented in hardware, software (including portable software, such as applets), or both. Further, connection to other computing devices such as network input/output devices may be employed. Software of computer system 200 may include code 250 for implementing embodiments of the present invention as described herein.

As noted above, embodiments of the invention provide systems and methods to provide safe, secure and accurate point-to-point delivery of prescription and non-prescription drugs in the long-term home care or ambulatory care environment. These embodiments may be implemented in hardware and/or software on any one or more systems such as described above. More specifically, embodiments of the present invention comprise a secure drug dispensing unit and medication enclosure combined with wireless connectivity and software based on smart mobile phone technology. Such a dispensing unit, also referred to herein as a Secure, Control, and Enhance Medication Adherence (SCEMA) system, can comprise a compact, wirelessly-controlled vessel or medication cartridge that can be securely sent either to, or returned from, the user's home using standard mail or other delivery services with a significantly lower risk of successful breech or diversion. According to one embodiment, the dispensing unit can use biometric identification and secure wireless network data services to track the location of the unit and, upon reaching its location, dispense the proper medications, in the prescribed manner, time and dose and do so solely to the (biometrically identified) authorized user.

Depending upon the implementation, the dispensing unit can of safely store days, weeks or months of an individual's prescription medication using multi-dose medication packaging (when appropriate) or other packaging methods to be dispensed when it is being operated by an authorized user that's been biometrically identified by the system. In some implementations, the dispensing unit can be equipped with audiovisual alerts to remind the user when to take their medication and can be implemented in an variety of form-factors ranging from a small travel-size unit to larger desktop units for home or office use, either with or without refrigeration. A user can then seamlessly access any one of multiple dispensing units (at home, work or during travel) depending on their needs and location by using their biometric identity. According to one embodiment, a centralized tracking system can prevent duplicate drug dispensing from occurring for this user when this type of configuration is employed.

According to one embodiment, associated software can be executed by a server or other computer accessible by a wireless network that communicates with the dispensing device and coordinates and tracks medication use, security, delivery, refills and adjudicates drug interaction information in order to reduce the incidence of adverse drug reactions. Such a system can permit automated, electronic transaction-based billing for the medications as they are used. Using such a system the user can be billed for the medication as they are used, not upon ordering or receipt of the dispensing vessel, thus eliminating the financial burden of front-loaded drug costs to the user. Using this dispensing strategy, the vessel essentially becomes an extension of the suppliers inventory storage system. The "sale" takes place upon consumption.

According to one embodiment, a lock-out system comprising an accelerometer and controlling software within the dispensing unit can engage a physical locking mechanism located on the dispenser. For example, the locking mechanism can be engaged by the software of the dispensing unit upon detecting impacts to the dispensing unit suggesting an attempt to forcibly open the unit. Additionally or alternatively, the locking mechanism can be triggered remotely through wireless communication. For example, it can be triggered by the centralized control software at any time the accelerometer or the location-tracking system indicates that the vessel is being diverted, or there's an attempt to breach the vessel. In some implementations, the vessel or medication cartridge of the dispensing unit can additionally or alternatively comprises a content disabling mechanism. For example, this mechanism may be provided when storing and dispensing classes of drugs that are particularly hazardous in the event of diversion and/or with a high incidents of diversion. This mechanism can comprise a safe, non-toxic method to render the pharmaceutical contents of the vessel or medication cartridge unusable in the event of a diversion or an attempt to forcibly open or breach the vessel or medication cartridge. The disabling mechanism can be triggered remotely through wireless communication or automatically. It can be triggered by the centralized control software at any time the accelerometer or the location-tracking system indicates that the vessel or medication cartridge is being diverted, or there's an attempt to breach the vessel or medication cartridge.

As noted, a biometrics system of the dispensing unit, such as a finger swipe reader, or other biometric device, can be employed to provide a reliable, compact, low-cost means of secure access to medications stored therein. The dispensing unit can thus provide for loading and dispensing the contents of the vessel or medication cartridge once the drug user has been positively identified using biometrics. It can also be used during loading of the vessel or medication cartridge by the drug supplier or by a caregiver, depending on the class of drug and the associated risk as well as regulations. For example, during the loading procedure the dispensing unit can scan and track the type and quantities of pharmaceutical products as they are loaded and verify them against the electronically stored prescription details. When dispensing the reverse scanning function takes place and permits information about the type and dosage of the drug to be displayed on the dispensing unit's display. Scanning can be accomplished through the use of a 3D barcode scanner embedded in the dispenser or other imaging or sensing methods.

Figure 3:
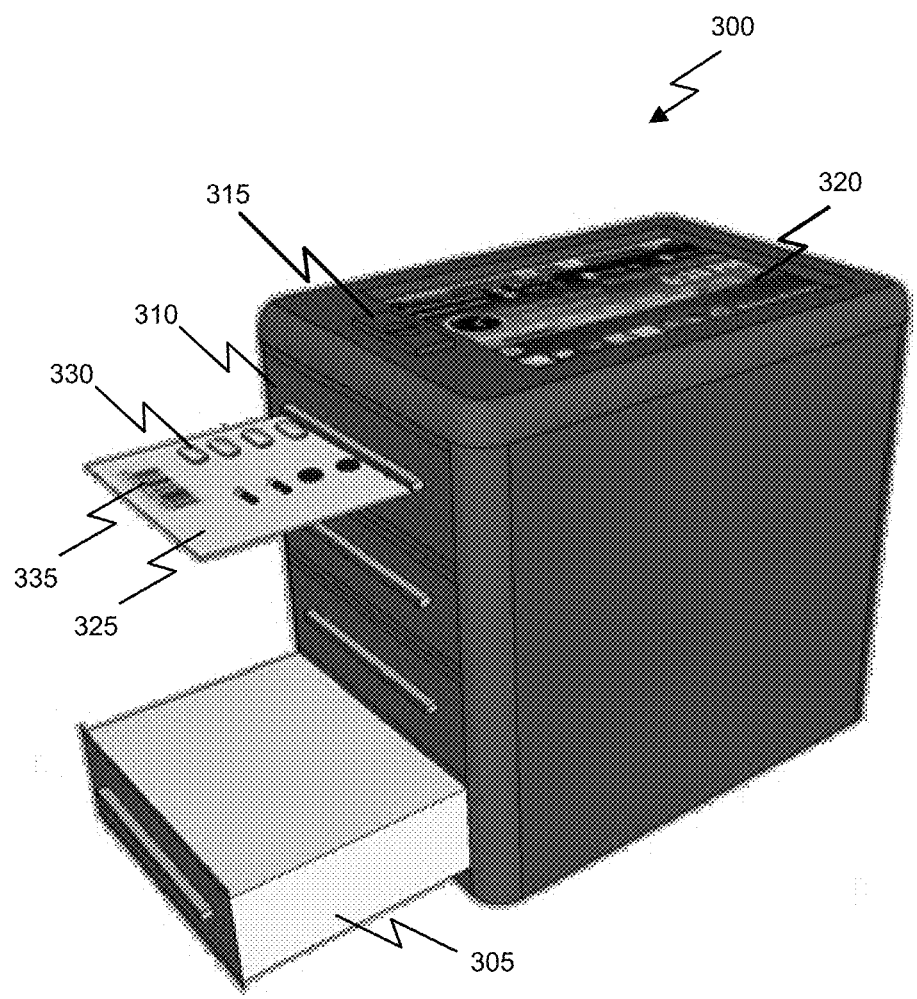
FIG. 3 is an illustration of a dispensing unit for use in a system to secure, control, and enhance medication adherence according to one embodiment of the present invention.

FIG. 3 is an illustration of a dispensing unit for use in a system to secure, control, and enhance medication adherence according to one embodiment of the present invention. Generally speaking, the dispensing unit 300 can comprise a wireless device such as any of the devices described above with reference to FIGS. 1 and 2. That is, the dispensing unit 300 can comprise a processor, memory, and wireless transceiver (not shown here for the sake of clarity) and may execute software to perform the functions described here. As illustrated here, the dispensing unit 300 can also include a number of removable vessels or medication cartridges 305 and 310. As will be seen, these vessels or medication cartridges 305 and 310 can be pre-loaded by a pharmacy with prescription medication for the user of the dispensing unit 300.

The dispensing unit 300 can also include one or more buttons 315 for initiating and/or operating dispensing and/or loading functions of the dispensing unit 305. In some cases, the button 315 can comprise of include a biometric reader, such as a fingerprint scanner, to read biometric information of an operator of the dispensing unit to be used to authenticate the user before dispensing or loading of medication from or into the dispensing unit 300. For example, at a scheduled time, an alarm may sound through a speaker (not shown here) of the dispensing unit 300. In response, the user can touch the button which may also take a biometric sample to be verified and, assuming the user is authenticated, a medication packet 325 containing the prescribed medication 330 to be taken and this scheduled time can be dispensed from one of the medication cartridges 310 of the dispensing unit 320.

The dispensing unit can also include a display 320 such as an LCD for displaying information related to the medication and/or functions of the dispensing unit 300. For example, the display 320 may show a schedule for dispensing medication, types of medications in the cartridges 305 and 310 currently loaded in the dispensing unit 300, an amount of medication remaining in the medication cartridges 310, etc. In some cases, the display 320 may comprise a touch screen providing access to other functions and features of the dispensing unit including but not limited to, setting and silencing alarms, initiating and/or canceling dispensing and/or loading operations, requesting refills, etc.

However in use a typical use, operation of the dispensing unit 300 can be reduced to a single user function specifically, placing a finger on a single button-like surface 315. The other operations that take place both before and after that event—from the dispensing unit 300 scanning the user's fingerprint, matching it to the one in a database, and dispensing the appropriate drugs from the medication cartridge 310, after they are themselves identified by the dispensing unit 300 through the data stored, for example, on an encrypted memory chip in the cartridge 310, are invisible to the user. Besides pressing this dispensing button 315, the user may also need to remove and replace the cartridges 305 and 310 in the dispensing unit 300. The level of technical complexity here is also very low, essentially equivalent to inserting or ejecting a video cassette tape or a DVD. But even this task can be performed (e.g., for an elderly user) by a professional or family care giver since a cartridge 305 can be designed to hold up to many days of medication and since multiple cartridges are employed, so it only has to been done approximately periodically.

According to one embodiment, other settings and controls can be encoded into a memory chip embedded into each cartridge 305 and 310. In this way, the user of the dispensing unit 300 does not need to touch the display 320 or otherwise interact with the dispensing unit 300. Rather, the programming information used by the dispensing unit 300, including but not limited to patient identification, prescription details such as dosage and expiration dates, etc., can be stored on the memory chip of the medication cartridges 305 and 310 in an encrypted format by the pharmacist or care provider, and can be updated remotely if necessary or appropriate. When a medication cartridge 305 is loaded into the dispensing unit 300 the information on the memory chip of that medication cartridge 305 can be read and the information can be used to program the actions of the dispensing unit. The patient's electronic fingerprint information can be collected once at the pharmacy or at the care provider's office, stored as part of the patient's permanent file, and reused for subsequent prescriptions and refills, i.e., to be stored in the memory of the cartridges to identify the intended recipient and this for control by the dispensing unit 300.

According to one embodiment, the dispensing unit 300 can also support multi-drug capabilities for support of dynamic, complex and multi-provider medication regimens. The use of unit dose packaging in the cartridges 305 and 310 accommodates complex drug regimens. Such packaging equipment permits several different drugs to be placed in a single packet, and the automated pharmacy equipment permits the packaging of sequential packets with different regimens in a given cartridge 305 should it be necessary to include additional drugs in two or more packets. In this case the dispensing unit 300 can dispense the additional packets in sequence. Also, a multi-cartridge design of the dispensing unit 300 can permit prescription modifications from the same, or other, providers without having to change the initial cartridge. For example, if a second, short-term prescription for an antibiotic is ordered by a physician it can be added to the patient's drug regimen by dispensing it from a second (third or fourth) cartridge. Long term changes can be handled in the same way, except that once the primary cartridge's contents is exhausted it can be refilled with the new drug added to the single packet regimen. Also, multiple cartridges permits prescription refills prior to the primary cartridge becoming empty. The refill cartridge can be placed in the dispensing unit 300 but not used until the primary is empty. The refill can then become the primary and the empty can be returned to the pharmacy for refill. This dispensing management can be handled automatically by the dispensing unit 300 by matching the contents of the individual cartridge(s) with the patient's prescription and dispensing what is appropriate, avoiding duplicate dispensing, reordering cartridges as they approach empty, and dispensing from multiple cartridges when appropriate to fill the ordered prescription(s).

According to one embodiment, the dispensing unit 300 can additionally or alternatively manage prescription and OTC drug compatibility. The addition of this capability can be facilitated by the multiple cartridge design of the dispensing unit 300 if implemented as such. That is, multiple cartridges can be loaded with prescription and OTC drugs but dispensed only in an order, combination, or on a schedule that does not create compatibility or interaction problems. Information for identifying and managing these compatibility or interaction problems can also be encoded into the on-board memory of the individual cartridges by the pharmacy or caregiver before being dispensed.

According to one embodiment, the dispensing unit 300 can additionally or alternatively provide medication reminders to promote medication adherence. In such cases, automated audio-visual medication reminders can be delivered by the display 320 on the top of the dispensing unit 300 and/or a mobile device that has a software application installed that enables the mobile device to communicate with the dispensing unit wirelessly, e.g., via Bluetooth, WiFi, etc. The medication reminders can be programmed through the pharmacy and delivered on the memory chip embedded in the cartridge. In some cases, these reminders can also be remotely updated by the pharmacy wirelessly, e.g., via a cellular, WiFi connection to the Internet, or other connection, in the event of prescription changes. In some cases, the audio-visual capabilities of the dispensing unit 300 can be used to deliver educational materials and provide a venue for virtual doctor's visits through the use of text messaging, voice messaging or live conferences.

According to one embodiment, the dispensing unit 300 can additionally or alternatively provide medication adherence monitoring and keep the professional provider/caregiver in the communication "loop." As described above, the system is capable of communicating wirelessly with the pharmacy via a cellular transceiver of the dispensing unit and/or via a WiFi or other connection from the dispensing unit 300 to the Internet or other communications network. In the event that dispensing unit detects the drugs have not taken as scheduled, the dispensing unit 300 can notify either the pharmacist, provider and/or caregiver. This can be accomplished an app loaded on the healthcare provider's or the pharmacist's smart phone, via a text message or email, or thorough other messages. Another feature that can be incorporated in the dispensing unit 300 to encourage adherence are game-like software features that track and score patient's adherence performance over time and offer feedback and other benefits and awards for top performers.

According to one embodiment, the dispensing unit 300 can additionally or alternatively support delivery validation functions to provide point-to-point safe and secure medication delivery, refills and returns. In such implementations, the dispensing unit 300 can notify the pharmacy and/or provider or caregiver when a new cartridge 305 is delivered, when it has been loaded in the dispensing unit 300, when the user dispenses medication and when the contents of a cartridge 305 is about to be exhausted, and thereby providing an automated refill request. The refill of the cartridge 305 can be safely and effectively accomplished using the secure cartridges as described herein. These allow the drug provider to ship a self-address envelop with the cartridge 305. When empty, or at the end of use (and unused drugs are still contained in the cartridge 305) the patient can place the cartridge 305 into the envelope and drops it in a mailbox. The pharmacy can then refill the cartridge 305 (or the unused drugs are safely disposed of) and the data stored in the memory of the cartridge 305 can be updated at the pharmacy and the cartridge 305 can be returned to the patient by the same method.

According to one embodiment, the dispensing unit 300 can additionally or alternatively provide automated loading and dispensing that allow pharmacy-level expertise to properly provision the system. In such implementations, rather than requiring the user, friends and/or family members to laboriously load drug dispensing chambers with a complex prescription regimens, the dispensing unit 300 uses the preloaded cartridges 305 and 310 that have been filled by professional pharmacy personnel using automated packaging systems. This not only prevents mistakes in the drug provisioning process but also prevents drug diversion and abuse that is a natural byproduct of an open, unsecured container and manual drug handling and loading in the home.

According to one embodiment, the dispensing unit 300 can additionally or alternatively provide Adverse Drug Reaction (ADR) adjudication functions which can comprise an interlock that proactively prevents ADR events and notifies providers should the system (e.g., using a third party ADR database) detect a potential ADR event. For example, the dispensing unit 300 can prevent the dispensing of the offending product(s) and notify the pharmacist or provider through wireless communication. In the meantime, the dispensing unit 300 can continue to dispense the standard regimen as it awaits updating. In some cases, an authorized pharmacist or provider may over-ride the ADR interlock remotely after the potential ADR case has been reviewed and approved. Facilitating professional overriding of these alerts can be provided in cases where clinical situations mandate use of drugs with interaction risks (e.g., spironolactone and ACE inhibitors in heart failure).

According to one embodiment, the dispensing unit 300 can additionally or alternatively provide biometric and barcode confirmation functions including matching the patient with the medication before dispensing. Positive patient identification permits both safe and effect drug dispensing and also prevents accidental (or intentional) multiple dose events. It also prevents drug diversion and abuse by family members. The biometric capabilities of the dispensing unit 300, coupled with the unit's 300 communication abilities, also allows for multi-point dispensing scenarios. For example, a user can maintain one dispensing unit 300 at home and another in their place of employment. From the perspective of the systems monitoring and/or controlling these dispensing units, these units can be coupled and viewed as a single dispensing unit, so that drugs dispensed on one unit are not dispensed again at another. Accordingly, an adherence record can be kept and continuously updated and synchronized across multiple systems and users.

According to one embodiment, the dispensing unit 300 can additionally or alternatively provide functions supporting the return of unused drugs. Using the secure cartridges described herein to securely and safely close the delivery loop, the safe return of unused or expired drugs to the pharmacy, or other points of disposal, can be effectively accomplished. As with the automated refill capabilities described above, this feature allows the drug provider to ship a self-address envelop with the cartridge. At the end of the prescription the patient can place the cartridge containing the unused contents into the envelope and drop it in a mailbox. Since all of the drugs in the system are tracked using both the bar code on the packets and the memory on the cartridge, the system can accounted for the doses loaded and dispensed, verses what has been returned.

Figure 4:
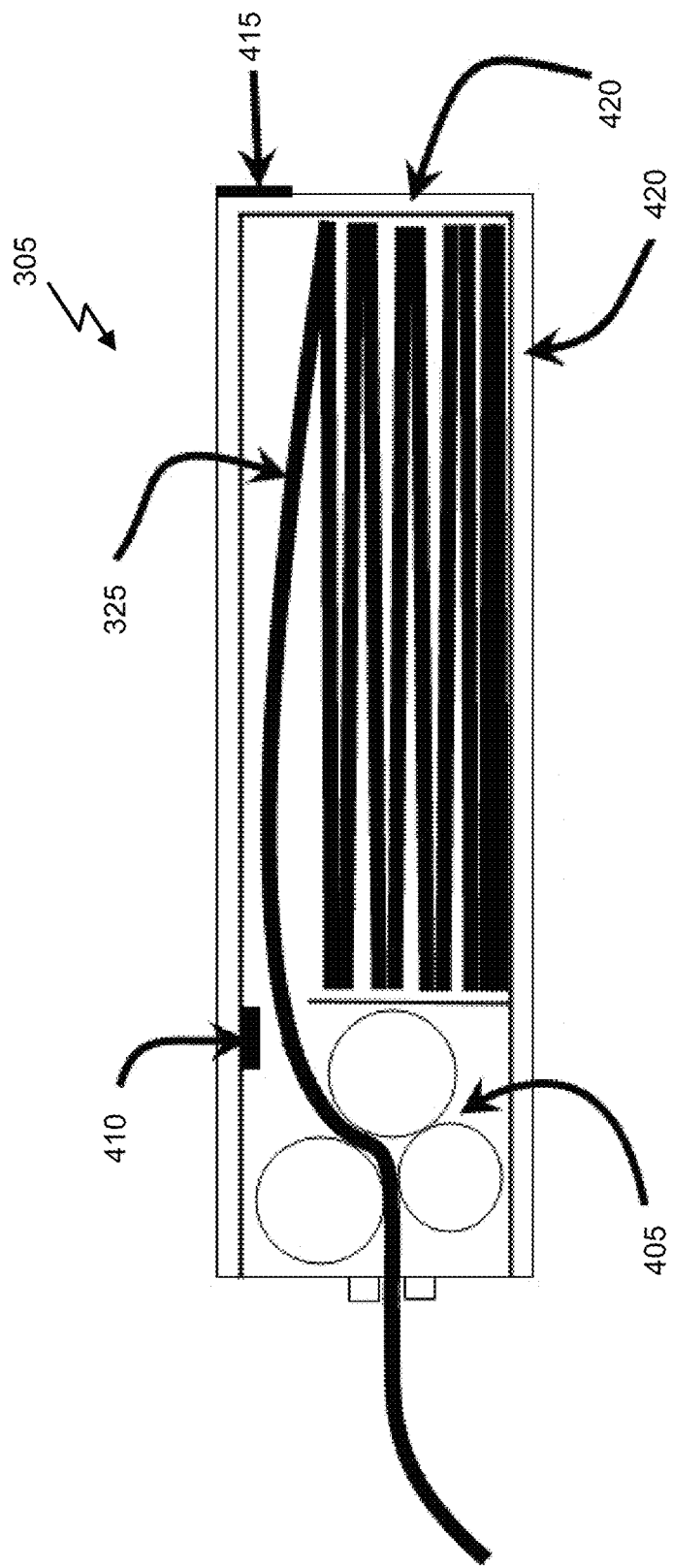
FIG. 4 is a cross-sectional view illustrating additional details of an exemplary secure medication cartridge for use in a dispensing unit such as embodied in FIG. 3.

FIG. 4 is a cross-sectional view illustrating additional details of an exemplary secure medication cartridge for use in a dispensing unit such as embodied in FIG. 3. Generally speaking, a dispensing unit as described above can comprise the main hardware component of the system. As noted, each dispensing unit can be adapted to accommodate one or more secure cartridges. These cartridges can serve as secure vessels that can transport drugs to the patient's home using standard mail or other delivery services with a low risk of successful breech or diversion. This same secure cartridge can also permit unused drugs to be returned to suppliers for safe disposal.

As illustrated here, the cartridge 305 can be preloaded by a pharmacy or other provider with drug packets 325 as described above. The cartridge 305 can comprise a feeder mechanism 405 including but not limited to a set of rollers or other mechanisms to provide a controlled feeding of the dug packets out of the cartridge 305. The feeder mechanism may be driven by a motor (not shown here) within the cartridge 305 or within the dispensing unit. In other cases, the feeder mechanism 405 may be manually advanced by the user but locked/unlocked by the cartridge 305 and/or dispensing unit under control of the various functions described herein.

Also as illustrated here, the cartridge 305 can include a barcode scanner 410 or other reader (e.g., an RFID reader). As noted above, each dose of the drug packets 325 can be marked or encoded with a barcode, RFID transducer, or other identification device. As the drug packet 325 doses are fed from the cartridge 305, the barcode reader 410 or other reader can read the barcode or other identification device and the dispensing unit can use this information to confirm and/or track the doses dispensed.

As illustrated here, the cartridge 305 can also include a memory 415 or chip. For example, the chip may in some cases comprise a processor as well as a memory depending upon the exact implementation. As noted above, the memory 415 of the cartridge 305 can store information used by the dispensing unit, including but not limited to patient identification, prescription details such as dosage and expiration dates, etc., in an encrypted format. Such information can be stored in the memory 415 by the pharmacist or care provider, and can be updated remotely by the pharmacist or care provide through a wireless communications link of the dispensing unit if necessary or appropriate. When a cartridge 305 is loaded into the dispensing unit the information on the memory chip 415 of that cartridge 305 can be read and the information can be used to program the actions of the dispensing unit. The patient's electronic fingerprint information can be collected once at the pharmacy or at the care provider's office, stored as part of the patient's permanent file, and reused for subsequent prescriptions and refills, i.e., to be stored in the memory 415 of the cartridges 305 to identify the intended recipient and this for control by the dispensing unit.

According to one embodiment, the cartridge 305 can also be equipped with a drug disabling feature that's triggered by tampering or an attempt to breach the container. In such embodiments, the cartridge 305 can include a chamber or reservoir 420 within the cartridge 305 filled with distilled water or other liquid capable of dissolving the drug packets 325. This reservoir 420 can be constructed to withstand normal handling but also to rupture upon sever shocks or attempts to breech the cartridge 305. This feature can comprise a small, embedded reservoir 420 built into an internal compartment within the cartridge 305. Any attempt to force open a cartridge (through cutting, fracturing or prying) results in the breach of this internal reservoir 420 and the release of the distilled water or other liquid into the interior of the cartridge 305, thereby immersing the unit dose packaged drugs contained within. As suggested by the illustration here, the reservoir 420 may substantially encompass or cover the inside of the cartridge 305 but other arrangements are contemplated and considered to be within the scope of the present invention. Once ruptured, the reservoir 420 releases its content and the released water or other liquid then dissolves the plastic packaging of the drug packets 325 and the drugs contained in the packet, rendering them all but useless.

The reservoir 420 can be considered an optional feature that can be installed, for example, on those cartridges designed to dispense drugs that are at high risk of being diverted and abused (e.g., Schedule II controlled substances). The drug packets 325 to be dispensed from the cartridge can use packaging material, a type of plastic (polyvinyl) commonly used for environmentally friendly consumer product packaging, that dissolves upon contact with water. This material, while highly stable in normal atmospheric moisture and temperature conditions, begins dissolving rapidly upon contact with liquid water. Using such materials, packet breach, and thereby exposure of the drugs to the water, can occur within a few seconds of exposure to distilled water at room temperature (approximately 20 degrees C.). Substantially complete dissolution of the package occurs in less than one minute under the same conditions. The resulting "drug soup" can be retained within the cartridge 305, where it will have very limited use or value for illicit drug applications thereby deterring future attempts to divert drugs in this manner. Safe disposal can then take place at the point of supply.

Figure 5:
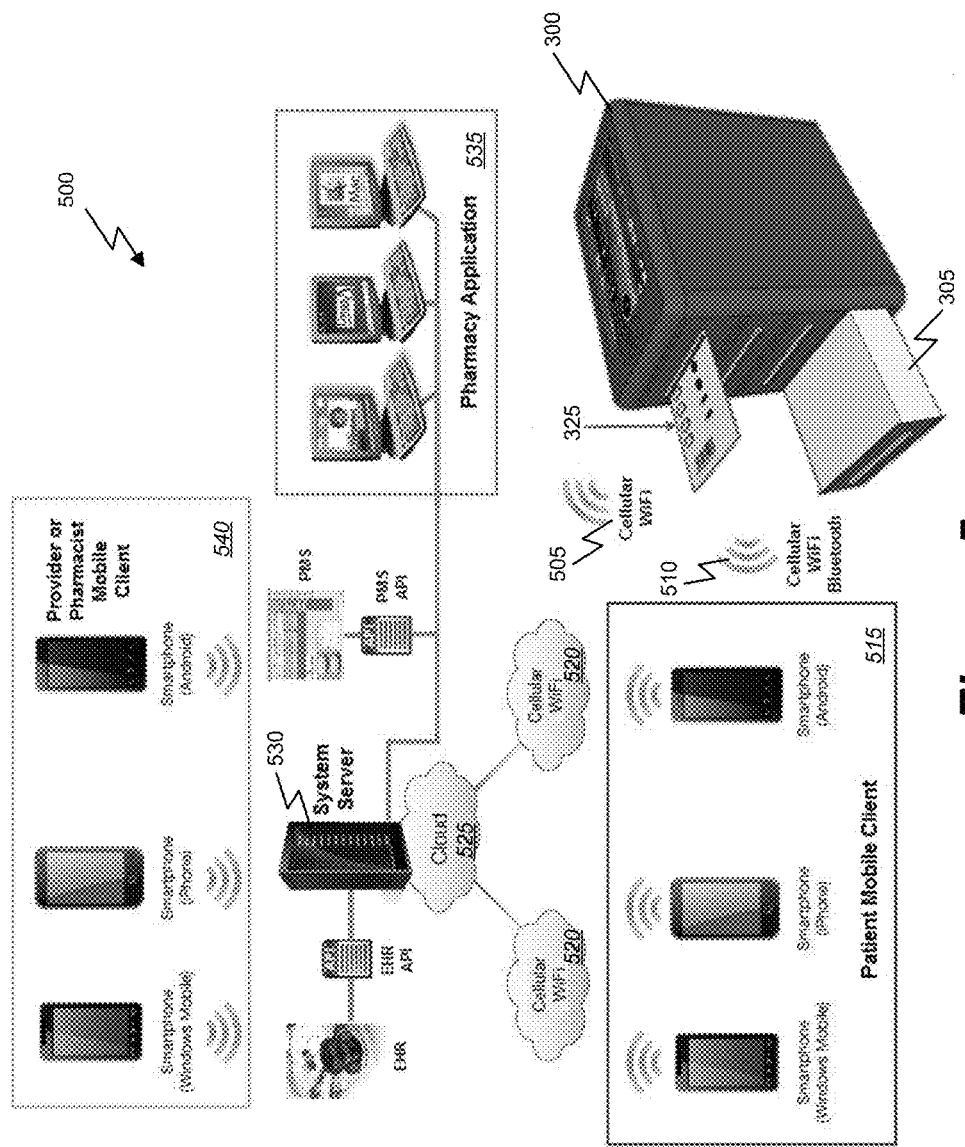
FIG. 5 is a block diagram illustrating, at a high level, elements of a system to secure, control, and enhance medication adherence according to one embodiment of the present invention.

FIG. 5 is a block diagram illustrating, at a high level, elements of a system to secure, control, and enhance medication adherence according to one embodiment of the present invention. As noted above, a dispensing unit 300 as described herein can comprise the main component for delivering medications to the user but can be used within a broader system 500 for monitoring, controlling, and tracking of the medication and its use. The dispensing unit can be communicatively coupled with one or more other elements of the system 500 via one or more communication channels 505 and 510 including but not limited to Bluetooth, WiFi, cellular, etc., depending upon the transceivers built into the dispensing unit 300 for a particular implementation.

For example, the system 500 can include one or more patient devices 515 such as a mobile phone, tablet, laptop etc., which can be communicatively coupled with the dispensing unit 300 through one or more of the communication channels 505 and 510 such as Bluetooth or WiFi. These one or more devices 515 can execute applications for interfacing with the functions of the dispensing unit 300 and/or other elements of the system 500. For example, through an interface of such an application on one or more of these devices 515, a user can receive alarms or reminders, check remaining supplies of medication, request refills, receive and/or set billing information, communicate with a pharmacist or care provider, etc.

Additionally or alternatively, the dispensing unit 300 can communicate wirelessly with one or more networks 520 and 525 extending beyond the user's location such a cellular or WiFi connection to the Internet. Through such networks 520 and 525, the dispensing unit 300 can communicate with one or more servers 530 executing applications for monitoring, controlling, and tracking of the dispensing unit 300, cartridges 305, and medication packets 325. For example, the server 530 can communicate with existing EHR, hospital information systems, and/or pharmacy management systems 535. Together, these systems can support tracking the dispensing of medication cartridges, tracking the return of unused portions of those cartridges, tracking the dispensing of medications from the dispensing unit, billing for the medications dispensed from the dispensing unit, provisioning patient information to the memory of dispensed medication cartridges, communicating changes or other control functions to the dispensing unit, etc.

Additionally or alternatively, the system 500 can include one or more devices 540 such as a mobile phone, tablet, laptop etc., used by one or more pharmacists, care providers, etc. These devices 540 can be communicatively coupled with the server 530 and/or the pharmacist system 535 via any of a variety of available communication channels including but not limited to Bluetooth, WiFi, cellular, etc. Generally speaking, these devices 540 can execute one or more applications allowing a pharmacist, doctor, or other care provider to interact with the functions provided by the server 530, pharmacist system 535, and/or the dispensing unit 300. For example, an application executing on a device 540 used by a doctor or other care provider can provide for monitoring use of the medications of the dispensing unit, providing updates to the dispensing unit 300 and/or pharmacy system 535 for adjusting the prescriptions as dispensed by the dispensing unit 300, etc. In another example, an application executing on a device 540 used by a pharmacist can provide for monitoring use of the medications of the dispensing unit 300, providing updates to the dispensing unit 300 for adjusting the prescriptions as dispensed by the dispensing unit 300, reading biometric information from the user of the dispensing unit 300 for provisioning same to the memory of cartridges dispensed by the pharmacy, etc.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A medication dispensing unit, comprising:
a processor;
a memory coupled with and readable by the processor and storing a set of instructions which, when executed by the processor, cause the processor to perform a plurality of functions controlling the dispensing of medication from the medication dispensing unit;
one or more wireless transceivers coupled with the processor,
wherein the medication dispensing unit is adapted to:
receive a plurality of removable, secure medication cartridges, the plurality of medication cartridges each comprising a medication cartridge memory storing information related to medication packets preloaded in the medication cartridge and an intended user of the medication;
accept the plurality of removable, secure medication cartridges preloaded with the medication packets; and
dispense the medication packets from the plurality of medication cartridges under control of the plurality of functions, wherein the plurality of functions includes one or more functions for changing prescriptions for dispensing the medication based on the different preloaded medications and instructions received by the medication dispensing unit via the one or more wireless transceivers.

2. A medication dispensing unit, comprising:
a processor;
a memory coupled with and readable by the processor and storing a set of instructions which, when executed by the processor, cause the processor to perform a plurality of functions controlling the dispensing of medication from the medication dispensing unit;
one or more wireless transceivers coupled with the processor, wherein the medication dispensing unit is adapted to:
receive a plurality of removable, secure medication cartridges, the plurality of medication cartridges each comprising a memory storing information related to medication packets preloaded in the medication cartridge and an intended user of the medication;
accept the plurality of removable, secure medication cartridges preloaded with the medication packets, wherein the medications preloaded in each of the plurality of medication cartridges are the same; and
dispense the medication packets from the plurality of medication cartridges under control of the plurality of functions, wherein the plurality of functions includes one or more functions for affecting a refill by switching from a primary cartridge for dispensing medication to a secondary cartridge for dispensing medication when the primary cartridge becomes empty.

3. A medication dispensing unit, comprising:
a processor;
a memory coupled with and readable by the processor and storing a set of instructions which, when executed by the processor, cause the processor to perform a plurality of functions controlling the dispensing of medication from the medication dispensing unit;
one or more wireless transceivers coupled with the processor,
wherein the medication dispensing unit is adapted to:
receive a plurality of removable, secure medication cartridges, the plurality of medication cartridges each comprising a medication cartridge memory storing information related to medication packets preloaded in the medication cartridge and an intended user of the medication;
accept the plurality of removable, secure medication cartridges preloaded with the medication packets, wherein the medications preloaded in each of the plurality of medication cartridges are different; and
dispense the medication packets from the plurality of medication cartridges under control of the plurality of functions, wherein the plurality of functions includes one or more functions for:
identifying a compatibility or interaction problem based on data that is encoded into the memory of the plurality of removable, secure medication cartridges, and
preventing dispensing of medication in an order, schedule, or combination that creates the compatibility or interaction problem based on data that is encoded into the memory of the plurality of removable, secure medication cartridges.

4. The medication dispensing unit of claim 3, wherein the plurality of functions includes one or more functions for providing a reminder to a user of a schedule for taking the medication based on the information stored in a memory of a medication cartridge of the plurality of medication cartridges related to the medication packets preloaded in the medication cartridge.

5. The medication dispensing unit of claim 4, wherein the plurality of functions includes one or more functions for updating the schedule based on instructions received by the medication dispensing unit via the one or more wireless transceivers.

6. The medication dispensing unit of claim 4, wherein the plurality of functions includes one or more functions for providing a notification via the one or more wireless transceivers when the medication dispensing unit detects the medication has not been taken as scheduled.

7. The medication dispensing unit of claim 4, wherein the plurality of functions includes one or more functions for providing a refill request via the one or more wireless transceivers when the medication dispensing unit detects the medication preloaded in the medication cartridge is low.

8. The medication dispensing unit of claim 3, further comprising a barcode reader, wherein the barcode reader reads a barcode from the medication packets and the plurality of functions includes functions for matching the authenticated user to the medication packets based on the barcode.

9. A secure medication cartridge comprising:
a container preloaded with medication packets and fluid; and
a feeder mechanism within the container adapted to feed the preloaded medication packets from the container; wherein the medication packets are constructed of plastic.

10. The secure medication cartridge of claim 9, further comprising a reader device adapted to read information encoded on the medication packets, the information related to and identifying medication stored in the medication packets.

11. The secure medication cartridge of claim 9, further comprising a memory storing information related to the medication packets preloaded in the medication cartridge and an intended user of the medication.

* * * * *